(12) United States Patent
Zhu

(10) Patent No.: US 7,179,492 B2
(45) Date of Patent: Feb. 20, 2007

(54) TRADITIONAL CHINESE PHARMACEUTICAL FORMULATION FOR TREATMENT OF PARADENTOSIS&COMMA; PROCESS FOR PREPARATION AND USE THEREOF

(76) Inventor: Jianzhong Zhu, Room 503, No. 18, Shang Gang Qi Cun, Pudong New Area, Shanghai (CN) 200126

( * ) Notice: Subject to any disclaimer, the term of this patent is extended or adjusted under 35 U.S.C. 154(b) by 0 days.

(21) Appl. No.: 10/514,209

(22) PCT Filed: Aug. 19, 2002

(86) PCT No.: PCT/CN02/00576

§ 371 (c)(1),
(2), (4) Date: Nov. 9, 2004

(87) PCT Pub. No.: WO03/094941

PCT Pub. Date: Nov. 20, 2003

(65) Prior Publication Data

US 2005/0170009 A1    Aug. 4, 2005

(30) Foreign Application Priority Data

May 14, 2002   (CH) .................... 02 1 11656

(51) Int. Cl.
*A61K 36/40* (2006.01)
*A61K 36/43* (2006.01)
*A61K 36/484* (2006.01)
*A61K 36/804* (2006.01)

(52) U.S. Cl. .................. 424/549; 424/757; 424/771

(58) Field of Classification Search ............... None
See application file for complete search history.

(56) References Cited

U.S. PATENT DOCUMENTS 4,613,591 A * 9/1986 Aburada et al. ............ 514/34
5,833,994 A * 11/1998 Wheelock et al. ......... 424/198.1
5,866,160 A * 2/1999 Hong et al. ................ 424/451
2002/0114854 A1 * 8/2002 Jeng ........................... 424/764

FOREIGN PATENT DOCUMENTS

| CN | 1104089 A |   | 12/1993 |
| CN | 1100936 A | * | 4/1995 |
| CN | 1137925 A | * | 12/1996 |
| CN | 1262126 A | * | 8/2000 |

OTHER PUBLICATIONS www.1stchineseherbs.com/andrographis_green_chiretta. html—accessed Jul. 11, 2005.*
www.fzrm.com/plantextracts/Tokyo_Violet_Herb_extract. htm—accessed Jul. 11, 2005.*
www.yourdictionary.com/ahd/s/s0539300.html—accessed Jul. 11, 2005.*
web.archive.org/web/20010420041034/http://www.chem.leeds.ac.uk.People/CMR/moreco2.html (Apr. 2001).*

* cited by examiner

*Primary Examiner*—Susan Coe Hoffman
(74) *Attorney, Agent, or Firm*—Merchant & Gould P.C.

(57) ABSTRACT

This invention involves a traditional Chinese medical preparation, its preparation and use. The present Chinese medicine that treats periodontitis is a pharmaceutically acceptable oral preparation containing fleece-flower, dried rehmanria, licorice, fresh-water turtle shell, dogwood fruit, dodder seed, derla andrographis and Tokyo violet herb as active ingredients and supplementary material. By adopting supercritical $CO_2$ fluid extraction technique for some materials, the containing of the effective ingredients of the preparation are ensured. With a novel and reasonable formula and definite curative effects, this invention provides periodontitis sufferers with a reliable medicine.

7 Claims, No Drawings

TRADITIONAL CHINESE PHARMACEUTICAL FORMULATION FOR TREATMENT OF PARADENTOSIS, PROCESS FOR PREPARATION AND USE THEREOF

TECHNOLOGY FIELD

This invention relates to a traditional Chinese medical preparation, its manufacturing methods and use.

BACKGROUND TECHNOLOGY

Periodontitis is a kind of disease of high frequency which may not be avoided in any countries. As many as 98% of adults in China are suffering from this disease. There is still no effective medicine dealing with periodontitis till now.

Traditional Chinese medicine believes that "the condition of kidney determines the condition of bones," and "teeth are of the same composition as bones." If kidney Yin is feeble, bones cannot be nourished and, as a result, teeth become loose and unfixed, which causes powerless chewing. Feeble kidney induces stomach heat and the burst of internal heat, and swelling and pain of gum. The weakness of spleen causes a general decrease of physical function, unable to resist viruses. Therefore, periodontitis occurs frequently.

Modern medicine believes that there are two main factors that induce periodontitis. First of all, the balance of the increase and the decrease of oral cavity bacteria group, caused by internal and external factors, is broken. Aerobic and anaerobic bacteria that mainly induce diseases produce in huge amount so quickly that bacterium speckle accumulates, giving much toxic metabolite and bacterium toxin, which causes the infection of the periodontal organism. Secondly, immune system weakens and becomes imbalanced and the patient himself cannot restrain the damage of periodontal organism caused by main pathogenic bacteria; thus, symptoms such as immunity abnormality and periodontitis inflammation occur.

INVENTION DISCLOSURE

This invention focuses on, with the combination of Chinese and modern medical theory, giving a kind of medicine of scientific reasons that can treat the pathogeny and symptoms of periodontitis effectively.

The Chinese herbal preparation for treating periodontitis as disclosed in the present invention is a kind of pharmaceutically acceptable oral preparation containing fleece-flower, dried rehmanria, licorice, fresh-water turtle shell, dogwood fruit, dodder seed, derla andrographis (green chiretta or kariyt) and Tokyo violet herb as active ingredients and pharmaceutical supplementary material, the weight percentage of which are as follows: fleece-flower 18–25%, dried rehmanria 11–18%, licorice 3–7%, fresh-water turtle shell 11–17%, dogwood fruit 7–15%, dodder seed 4–11%, derla andrographis 4–12%, Tokyo violet herb 8–15%.

The "oral preparation" mentioned by this invention refers to the dosage form of hard capsule, soft capsule, tablet, pill, granule, oral liquid, etc.

Another technical problem to be solved by the present invention is to disclose the manufacturing method of the above-mentioned Chinese preparation by adopting modern extraction technology.

The method for preparing the Chinese herbal preparation for treating periodontitis of the present invention includes the step of obtaining the effective ingredients of fleece-flower, dried rehmanria, licorice, fresh-water turtle shell, dogwood fruit, dodder seed, derla andrographis and Tokyo violet herb, and the step of formulating said preparation by combining said effective ingredients with pharmaceutical supplementary material. In an preferable embodiment, the effective ingredients of fleece-flower, dried rehmanria, fresh-water turtle shell, dogwood fruit, dodder seed and derla andrographis are obtained by supercritical $CO_2$ fluid extraction.

In a more preferable embodiment, said manufacturing method disclosed in the present invention includes the following steps.

i Production of the Extractants of the Effective Ingredients of Derla Andrographis According to the prescription amount, dry, crush and pass the derla andrographis leaves through 20 Mesh screen, and then put into the airtight extraction cauldron under the pressure of 18–32 Mpa and the temperature of 28–45° C. The $CO_2$ flow is 800 ml/h–1250 ml/h and 70–99% alcohol is used with the circulation of 80 ml/h–125 ml/h. After 2–4 hours, decrease the pressure and take the extractants out; dry and crush the dregs into 220–280 Mesh powder and reserve for use.

ii Production of the Extractants of the Effective Ingredients of Dried Rehmanria, Fresh Water Turtle Shell, Fleece-Flower, Dodder Seed, Dogwood Fruit According to the prescription amount, mix dried rehmanria, fresh water turtle shell, fleece-flower, dodder seed, dogwood fruit and crush them into 40 Mesh. Put them into the first level extraction cauldron under the pressure of 8–18 Mpa and the temperature of 52–70° C., with the $CO_2$ flow being 1000 ml/h–1500 ml/h and 65–85% alcohol is used with the circulation being 100 ml/h-150 ml/h. After 2–4 hours, lower the pressure to 8–15 Mpa and the temperature to 45–55° C., make it flow into separation column and then into analysis cauldron. After decreasing to the normal pressure, take the extractants out and collect the dregs for future use.

iii Production of the Active Ingredients of the Preparation

According to the prescription amount, crush licorice, Tokyo violet herb into 20 Mesh and put them, together with the dregs of step ii, into a reaction pot equipped with condenser. Decoct them for three times with water the amount of which is, respectively, 6, 4 and 2.5 times as many as that of the contents in the pot. Collect the volatile mixture of oil and water and remove the dregs, mix the mixture and decoct for 3 times. After filtration, add the mixture into the filtrate and stir it. The mixture is then concentrated under reduced pressure until the thickness ratio reaches 1–1.25. Then, the extractants of step 1 and 2 are added and the mixture are mixed, dried in low temperature, and crushed into 220–280 Mesh powder. The powder of derla andrographis of step i is added into said powder and then they are stirred even.

iv Formulation of Capsule, Tablet, Granule, Pill

The active ingredients of step iii are combined with pharmaceutical supplementary materials and the capsule, tablet, granule, pill, etc are made according to conventional manner.

v Production of Oral Liquid

According to the prescription amount, the derla andrographis is crushed into 20 Mesh, soaked in alcohol (70–99%, 10–25° C.), the amount of which is 10 times as much as that of the derla andrographis, in airtight condition for 24 hours.

The soaked liquid is separated by cycling alcohol via reflux, and the remaining liquid is reserved. The dregs are for later use.

According to the prescription amount, licorice, Tokyo violet herb, dried rehmanria, fresh-water turtle shell, fleece-flower, dodder seed, dogwood fruit are dried and crushed into 20 Mesh, and then are put, together with the dregs of derla andrographis, into a reaction pot equipped with condenser. The mixture is decocted for three times, each for 1.5 hours, with water the amount of which is respectively 8, 6, and 2 times as much as that of the contents in the pot. The volatile mixture of water and oil in the condenser is collected. Remove the dregs, mix and decoct for three times, add the extractants of derla andrographis into the filtrate. The filtrate is concentrated under decreased pressure at 60° C. till the concentration arrives 1.06–1.10. After cooling to 10–25° C., volatile mixture of water and oil and suitable amount of condiment and preservative are added.

However, it should be appreciated that the above preparation are merely one preferable embodiment for preparing the Chinese herbal preparation of the present invention. The skilled person in the art will suitably change each parameters, conditions and reagents based on the disclosure of the present invention. All these modifications are also included in the scope of the invention.

Another technical problem to be solved by the present invention is the use of the present Chinese herbal preparation in the production of a medicine for treating periodontitis.

This invention can be applied to symptoms induced by periodontitis such as gum inflammation, bleeding, festering, teeth loosening, ache, unable to chew, fever, headache, etc.

In the period of treatment of 2–7 days, a patient should take the medicine 3 times/day, 3 tablets/time; each tablet contains the herbal preparation 6.0–8.0 mg.

"Nourished by medulla, teeth, the end of bone, are dominated by kidney. Therefore, a deficient kidney leads to loose teeth, while great energy provides healthy teeth." (*Chinese Medicine of Sichuan* $11^{th}$ volume, $2^{nd}$ issue, pp 46). Currently, medicine used to treat periodontitis is mainly of antipyretic. It can not only control bacteria, virus, fungus, etc., but also neutralize virus." Its main effects include: "1, resist microbe that can induce diseases; 2, be against toxin of bacteria; 3, allay fever; 4, resist inflammation; 5, improve immunity system and the function of hypophosis." (Meng Qingyun, *Fifty Years' Development of Chinese Medicine in China*, 1999, pp 119–120).

Knowing the insufficiency of traditional antipyretic when treating periodontitis, this invention, attaching much importance to diminishing inflammation, cooling blood and relieving internal heat, nourishes liver, kidney, spleen and stomach at the same time. When controlling the number of bacteria, it also improves immunity against the bacteria that induce diseases, and reduce the possibility of becoming abnormal. It treats the symptoms of periodontitis by keeping the whole body in balance and controlling in a short time. That is to say, the condition of kidney determines the condition of bones and teeth are of the same composition as bones. If kidney Yin is feeble, bones cannot be nourished and, as a result, teeth become loose and unfixed, which causes powerless chewing. Feeble kidney induces stomach heat and the burst of internal heat, and swelling and pain of gum. The weakness of spleen causes a general decrease of physical function, unable to resist viruses. Therefore, periodontitis occurs frequently. Focusing on liver and kidney, fleece-flower and dried rehmanria nourish Yin and relieve heat. Dodder seed nourishes spleen, liver and kidney, doing good to all kinds of people: for the weak, it is nourishing; for the strong, it is profitable, for the cold, it is warm; for the damp, it is dry; for the dry, it is wet, so that it is nice to spleen, liver and kidney. The above three are the main medicine. Fresh-water turtle shell and dogwood are assistance for they help to limit Yang, releasing ache, relieving heat, sending away the motion of fidgety and making bones stronger. Tokyo violet herb and derla andrographis are of supplementary since they cool the blood, diminish inflammation and relieve internal heat. Licorice, nourishing kidney, stopping pain, relieving internal heat and balancing all the herbs, is the enhancer of the preparation. All the herbs cooperating, kidney Yin is nourished, liver is strengthened, spleen is improved, internal heat is relieved, blood is cooled, so that periodontitis is cured from both its symptoms and its root cause by herbs complementing each other.

Traditional Chinese medicine applies water-extraction and alcohol-extraction to the production of compound preparation. It requires a lot of time (about 6 days) and high temperature (100° C.). As a result, substances of effective ingredient that are unstable when heated are easily oxidized, decomposed, polymerized, and isomerized. Furthermore, the extract contains many impurities. In addition, some effective ingredients of large molecular weight can not be obtained by water extraction or alcohol extraction because of high boiling temperature and small volatility. This results in not only a lot of energy consumption, but also the lost of effective ingredients, affecting the therapeutic effect of the medicine.

This invention, however, adopts supercritical $CO_2$ fluid extraction to some raw materials, which requires a low temperature (about 25–45° C.), a shorter time (2–5 hours), less energy consuming and provides a stable quality without organic solution remaining in the preparation. As supercritical $CO_2$ fluid possesses high solubility for fat-soluble component, high penetration ability and high transferring rate, no effective ingredient is lost in the process of extraction. Meanwhile, the preparation being in the condition of unsaturated solution, effective ingredients are not oxidized, decomposed, polymerized or isomerized; all the components keep their own character as much as possible and the extraction is of a natural fragrance. In addition, under high pressure, supercritical $CO_2$ fluid can effectively and completely extract ingredients of large molecular weight, high boiling point and small volatility, for instance, plant polysaccharide and plant ester, average gaining rate being 3.5–4 times higher than traditional method. This method ensures the effect of the preparation and levels up that of herbs.

This invention, combining the method of solid fluid extract (>250 Mesh), makes it easy for people to take in the effective ingredients, raising the utility of the medicine.

Aiming at periodontitis, bezoar detoxification pills are know as an effective medicine of relieving heat, enjoying a large range of clinical use.

Taking bezoar detoxification pills set as controlled group, clinical test of the invention is conducted.

Test group: the preparation of the present invention, 700 mg/pill, dosage form: pill Controlled group: bezoar detoxification pills, 600 mg/pill Dosage: 700 mg*2pills/time, 3 times/day Period: 7 days, any other medicine is excluded Clinical manifestation: 1) gum inflammation, 2) gum ache, 3) gum bleeding, 4) teeth loosening, 5) teeth ache when biting lips Periodontitis parameters: gum index (GI), sulcus bleeding index (SBI), teeth pounched depth (PD), teeth move degree (MD)

Results:
1. After administration, test group has an evident improvement in GI, SBI, PD, MD (P<0.01); controlled group has an evident improvement in GI, SBI (P<0.01), but PD and MD have no outstanding improvement (P>0.05).
2. Comparison of clinical manifestation after administration

|  | Test Group | | | Controlled Group | | |
|---|---|---|---|---|---|---|
| Manifestation | Evident Improvement | Improvement | No Improvement | Evident Improvement | Improvement | No Improvement |
| 1 | 83.3% | 16.7% | 0 | 13.3% | 23.3% | 63.4% |
| 2 | 100% | 0 | 0 | 46.8% | 26.6% | 26.6% |
| 3 | 63.4% | 33.3% | 3.3% | 13.3% | 36.7% | 50% |
| 4 | 92.3% | 7.7% | 0 | 4.0% | 8.0% | 88% |
| 5 | 92.0% | 8.0% | 0 | 37.5% | 41.7% | 20.8% |
| Effectiveness |  | 86.20% |  |  | 22.98% |  |

As the result shows, this preparation can control periodontitis effectively in 2–7 days, having an better effect than bezoar detoxification pills.

When relieving heat, diminishing inflammation and cooling blood, this invention also nourishes liver, kidney, spleen and stomach; when controlling bacteria, this invention also upgrades people's immunity against bacteria that induce diseases; this medicine, looking into both symptoms and root cause of the disease, has an evident effect, providing a new effective and easily taken medicine for the treatment of periodontitis.

Specific Embodiments

EXAMPLE 1

Production of Active Ingredients of the Preparation i After drying, crushing and passing the derla andrographis leaves through 20 Mesh screen, put them into the airtight extraction cauldron under the pressure of 19.8 Mpa and 35° C., with the $CO_2$ flow being 820 ml/h and 78% alcohol circulation being 82 ml/h. After 4 hours, lower the pressure and take the extractants out; dry and crush the dregs into 220 Mesh powder and reserve for future use.

ii Mix the dried rehmanria, fresh water turtle shell, fleece-flower, dodder seed, dogwood fruit and crush them into 40 Mesh. Put them into the first level extraction cauldron under the pressure of 10 Mpa, 55° C., with $CO_2$ flow being 1180 ml/h and 78% alcohol circulation being 108 ml/h. After 3 hours, decrease the pressure to 10.8 Mpa and the temperature to 48° C., make it flow into separation column and then into analysis cauldron. Decrease to the normal pressure, take the extractants out and collect the dregs for future use.

iii Crush licorice and Tokyo violet herb into 20 Mesh and put them, together with the dregs of step ii, into a reaction pot equipped with condenser. Decoct them for three times with water, the amount of which is respectively 6, 4 and 2.5 times as much as that of the contents in the pot. Collect the volatile mixture of oil and water and remove the dregs, mix the mixture and decoct for 3 times. After filtration, add the mixture into the filtrate and stir it. Said mixture is concentrated under decreased pressure, until the thickness ratio arrives 1.25. Then, add the extractants of step i and ii into it and mix them, dry the mixture in low temperature and crush it into 220 Mesh powder. Add the powder of derla andrographis of step i and stir even.

EXAMPLE 2

Production of Sugarcoated Tablets

Formulation
Fleece-flower 20%, dried rehmanria 15%, licorice 5%, fresh-water turtle shell 15%, dogwood fruit 15%, dodder seed 11%, derla andrographis 8%, Tokyo violet herb 11%
With suitable amount of supplementary medicine, tablets of 700 mg/tablet are made.
According to the above formulation, the active ingredients of preparation are prepared according to the method of example 1, and pressed into tablets, coated with hot sugar powder, and make them into pills weighing 700 mg.

EXAMPLE 3

Production of Sapsule

Formulation
Fleece-flower 20%, dried rehmanria 15%, licorice 5%, fresh-water turtle shell 15%, dogwood fruit 15%, dodder seed 11%, derla andrographis 8%, Tokyo violet herb 11%.
With suitable amount of supplementary medicine, capsules of 350 mg/capsule are made.
According to the above prescription, the active ingredients of preparation are prepared as the method of example 1, and then are filled into capsule shells.

EXAMPLE 4

Production of Sugarcoated Pills

Formulation
Fleece-flower 20%, dried rehmanria 15%, licorice 5%, fresh-water turtle shell 15%, dogwood fruit 15%, dodder seed 11%, derla andrographis 8%, Tokyo violet herb 11%
Suitable amount of supplementary medicine i Dry, crush and pass the derla andrographis leaves through 20 Mesh screen, and put them into the airtight extraction cauldron under the pressure of 19.8 Mpa, 35° C., with $CO_2$ flow of 820 ml/h and 78% alcohol circulation of 82 ml/h.

After 4 hours, decrease the pressure and take the extractants out; dry and crush the dregs into 220 Mesh powder, reserving for use.

ii Mix dried rehmanria, fresh water turtle shell, fleece-flower, dodder seed, dogwood fruit and crush them into 40 Mesh. Put them into the first level extraction cauldron under the pressure of 10 Mpa, 55° C., with the $CO_2$ flow being 1180 ml/h and 78% alcohol circulation being 108 ml/h. After 3 hours, decreasing the pressure to 10.8 Mpa and the temperature to 48° C., make it flow into separation column and then into analysis cauldron. After decreasing to the normal pressure, take the extractants out and collect the dregs, reserving for use.

iii Crush licorice and Tokyo violet herb into 20 Mesh and put them, together with the dregs of step ii, into the reaction pot equipped with condenser. Decoct them three times respectively with 6, 4 and 2.5 times amount of water. Collect the volatile mixture of oil and water and remove the dregs, mix the mixture and decoct for 3 times. The mixture is filtered and the mixture of oil and water is added into the filtrate and stir it. Then, the mixture is concentrated under decreased pressure until the thickness ratio reaches 1.25. The extractants of steps i and ii are added into it and then mixed, dried under low temperature and crush into 220 Mesh powder. Add the powder of derla andrographis of step i and make the pills by machine, which weigh 700 mg every 8 pills.

EXAMPLE 5

Production of Oral Liquid

Formulation

Fleece-flower 20%, dried rehmanria 15%, licorice 5%, fresh-water turtle shell 15%, dogwood fruit 15%, dodder seed 11%, derla andrographis 8%, Tokyo violet herb 11%

With suitable amount of supplementary medicine, each bottle is formulated with 500 ml.

According to the prescription amount, crush the derla andrographis into 20 Mesh, soak it in 10 times amount of ethanol (78%, 25° C.) in airtight condition for 24 hours. Separate the soaked liquid, recover the ethanol via reflux, and reserve the remaining liquid and dregs respectively for later use.

According to the prescription amount, dry and crush licorice, Tokyo violet herb, dried rehmanria, fresh-water turtle shell, fleece-flower, dodder seed, dogwood fruit into 20 Mesh, and then put them, together with the dregs of derla andrographis, into the reaction pot with condenser. Decoct it for three times, each for 1.5 h, with 8, 6, 2 times amount of water respectively. Collect volatile mixture of water and oil in the condenser. Removing the dregs, mixing and decocting three times, add the extractant of derla andrographis into the filtrate. Concentrate the filtrate under decreased pressure at 60° C. till the thickness ratio reaches 1.06. Cooling it to 25° C., add thereinto the volatile mixture of water and oil and suitable amount of condiment and preservative.

EXAMPLE 6

Production of Dry Syrup (Granule)

Formulation

Fleece-flower 20%, dried rehmanria 15%, licorice 5%, fresh-water turtle shell 15%, dogwood fruit 15%, dodder seed 11%, derla andrographis 8%, Tokyo violet herb 11%

With suitable amount of supplementary medicine, granule of 15 g/bag is made.

i Drying, crushing and passing them through 20 Mesh, put the derla andrographis leaves into the airtight extraction cauldron of 50 L under 19.8 Mpa, 35° C., with $CO_2$ flow being 820 ml/h and 78% alcohol circulation being 82 ml/h. After 4 hours, decrease the pressure and take the extractants out; dry and crush the dregs into 220–280 Mesh powder, reserving for use.

ii Mix dried rehmanria, fresh water turtle shell, fleece-flower, dodder seed, dogwood fruit and crush into 40 Mu. Put them into the first level extraction cauldron under 10 Mpa, 55° C., with $CO_2$ flow being 1180 ml/h and 78% alcohol circulation being 108 ml/h. After 3 hours, decrease the pressure to 10.8 Mpa and the temperature to 48° C., and make it flow into separation column and then into analysis cauldron. Decreasing to the normal pressure, take the extractants out and collect the dregs, reserving for use.

iii Crush licorice and Tokyo violet herb into 20 Mu and put them, together with the dregs of step ii, into the reaction pot equipped with condenser. Decoct them three times respectively with 6, 4 and 2.5 times amount of water. Collecting the volatile mixture of oil and water and removing the dregs, mix the mixture and decoct 3 times. Filter and add the mixture of oil and water into the filtrate and stir them. Concentrate it with decreased pressure until the thickness ratio reaches 1.25, and then add the extractants of step i and ii into it and mix them, dry the mixture in low temperature and crush it into 220 Mesh powder. Add the powder of derla andrographis of step i and stir even. Granule is made and dried, pack into bag with 15 g/bag.

EXAMPLE 7

Production of Soft Capsule

Formulation

Fleece-flower 20%, dried rehmanria 15%, licorice 5%, fresh-water turtle shell 15%, dogwood fruit 15%, dodder seed 11%, derla andrographis 8%, Tokyo violet herb 11%

With suitable amount of supplementary medicine, capsules are made with 2500 mg per capsule.

i Drying, crushing and passing them through 20 Mesh, put the derla andrographis leaves into the airtight extraction cauldron of 50 L under 19.8 Mpa, 35° C., with $CO_2$ flow being 820 ml/h and 78% alcohol circulation being 82 ml/h. After 4 hours, decrease the pressure and take the extractants out; dry and crush the dregs into 220 Mu powder, reserving for use.

ii Mix dried rehmanria, fresh water turtle shell, fleece-flower, dodder seed, dogwood fruit and crush into 40 Mesh. Put them into the first level extraction cauldron under 10 Mpa, 55° C., with $CO_2$ flow being 1180 ml/h and 78% alcohol circulation being 108 ml/h. After 3 hours, decrease the pressure to 10.8 Mpa and the temperature to 48° C., make it flow into separation column and then analysis cauldron. After decreasing to the normal pressure, take the extractants out and collect the dregs, reserving for use.

iii Crush licorice and Tokyo violet herb into 20 Mesh and put them, together with the dregs of step ii, into the reaction pot equipped with condenser. Decoct them three times respectively with 6, 4 and 2.5 times amount of water. Collecting the volatile mixture of oil and water and removing the dregs, mix the mixture and decoct 3 times. Filter and add the mixture of oil and water into the filtrate and stir them. Enrich it, with decreased pressure, until the thickness ratio arrives 1.25. Add the extractants of step i and ii into it and mix them, dry the mixture in low temperature and crush it into 220 Mesh powder. Add thereinto the volatile mixture of oil and water and refined medicinal oil and then stir even. Add thereinto suspending stabilizer to formulate suspending liquor.

iv According the normal amount, mix gelatin, glycerine, anion water and pigment of medical use and stir even, getting mixed solution of the same solubility.

v Get the soft capsules by mixing colloidal liquid and suspending liquor in accordance with the fixed proportion, each of which weighs 700 mg. Dry the soft capsules under 40° C. and wash them in water-free solvent.

The invention claimed is:

1. A Chinese herbal preparation for treating periodontitis, wherein, said preparation is a pharmaceutically acceptable oral preparation consisting essentially of fleece-flower, dried rehmannia, licorice, fresh-water turtle shell, dogwood fruit, dodder seed, derla andrographis and Tokyo violet herb as active ingredients and optionally one or more pharmaceutical supplementary materials.

2. The Chinese herbal preparation for treating periodontitis according to claim 1, wherein, the weight percentages of said active ingredients in said preparation are: fleece-flower 18–25%, dried rehmannia 11–18%, licorice 3–7%, fresh-water turtle shell 11–17%, dogwood fruit 7–15%, dodder seed 4–11%, derla andrographis 4–12%, and Tokyo viole herb 8–15%.

3. The Chinese herbal preparation for treating periodontitis according to claim 1, wherein, said oral preparation is in the form of hard capsule, soft capsule, tablet, pill, granule, or oral liquid.

4. The Chinese herbal preparation for treating periodontitis according to claim 1, additionally comprising pharmaceutical supplementary material.

5. A method for preparing the Chinese herbal preparation for treating periodontitis of claim 1, including the step of obtaining the effective ingredients of fleece-flower, dried rehmannia, licorice, fresh-water turtle shell, dogwood fruit, dodder seed, derla andrographis and Tokyo violet herb, and the step of formulating said preparation by combining said effective ingredients with pharmaceutical supplementary material.

6. The method according to claim 5, wherein the effective ingredients of fleece-flower, dried rehmannia, fresh-water turtle shell, dogwood fruit, dodder seed and derla andrographis are obtained by supercritical CO2 fluid extraction.

7. A method of treating periodontitis comprising the step of administering an effective amount of the preparation of claim 1 to an individual in need of such treatment.

* * * * *